(12) United States Patent
Majeed et al.

(10) Patent No.: US 7,514,573 B2
(45) Date of Patent: Apr. 7, 2009

(54) PROCESSES FOR THE MANUFACTURE OF CHIRAL AND RACEMIC FORMS OF 3-AMINOTETRAHYDROFURANS, THEIR SALTS AND DERIVATIVES

(75) Inventors: Muhammed Majeed, Piscataway, NJ (US); Kalyanam Nagabhushanam, Piscataway, NJ (US); Sivaprskash Kurumanghat Balakrishnan, Bangalre (IN); Savita Ganjihal, Bangalore (IN); Rajendran Ramanujam, Bangalore (IN); Rattan Sood, Bangalre (IN); Subbalakshmi Prakash, Piscataway, NJ (US)

(73) Assignee: Sami Labs Ltd, Bangalore (IN)

( * ) Notice: Subject to any disclaimer, the term of this patent is extended or adjusted under 35 U.S.C. 154(b) by 56 days.

(21) Appl. No.: 11/733,772

(22) Filed: Apr. 11, 2007

(65) Prior Publication Data
US 2008/0255377 A1     Oct. 16, 2008

(51) Int. Cl.
*C07D 307/22* (2006.01)
(52) U.S. Cl. ..................................................... 549/480
(58) Field of Classification Search ................. 549/509, 549/480
See application file for complete search history.

*Primary Examiner*—Bernard Dentz
*Assistant Examiner*—David E Gallis

(57) ABSTRACT

A novel process for the synthesis of (S)-3-Amino-tetrahydrofuran and (R)-3-Amino-tetrahydrofuran is described. The process is applicable for substituted chiral-3-aminotetrahydrofuran derivatives.

8 Claims, No Drawings

PROCESSES FOR THE MANUFACTURE OF CHIRAL AND RACEMIC FORMS OF 3-AMINOTETRAHYDROFURANS, THEIR SALTS AND DERIVATIVES

BACKGROUND OF THE INVENTION

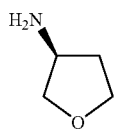
3-(S)-Aminotetrahydrofuran

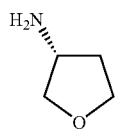
3-(R)-Aminotetrahydrofuran

3-Aminotetrahydrofurans form part of several pharmacologically active compounds. They seem to confer certain desirable properties on the investigational drug structures. A series of G-protein coupled adenosine receptors mediate cardiac and antilipolytic activities. In particular, selective adenosine A1 receptors have received attention for possible antiarrhythmic activity. For example, 3-(R)-aminotetrahydrofuranyl moiety formed an integrative structural feature of selective, high affinity adenosine A1 receptor agonists (Elzein, E; Kalla, R; Li, X; Perry, T; Marquart, T; Micklatcher, M; Li, Y; Wu, Y; Zeng, D and Zablocki, J, *Bioorg. Med. Chem. Lett.*, 2007, 77, 161). 3-Aminotetrahydrofuranyl moiety also formed part of structural features of orally bioavailable experimental CGRP receptor antagonists (Bell, 1 M; Bednar, R A; Fay, J F; Gallicchio, S N; Hochman, J H; McMasters, D R; Miller-Stein, C; Moore, E L; Mosser, S D; Pudvah, N T; Quigley, A G; Salvatore, C A; Stump, C A; Theberge, C R; Wong B K; Zartman, C B; Zhang, X-F; Kane, S A; Graham, S L; Vacca, J P and Williams, T M, *Bioorg. Med. Chem. Lett.*, 2006, 76, 6165). In spite of such extensive uses of 3-aminotetrahydrofuran in medicinal chemistry, methods to obtain chiral forms are scarce and hard to practice

RELATED PRIOR ART

Optically pure isomers of 3-aminotetrahydrofuran has been obtained through a lengthy sequence starting from L-malic acid. In this process L-malic acid is esterified to, say for example, dimethyl-L-malate which is reduced to a triol. The triol is highly water soluble and presents practical difficulty of isolation. The triol is then cyclized to give 3-(S)-hydroxy-tetrahydrofuran which, in turn, is esterified, for example with mesyl chloride. The resultant mesylate ester is then reacted with sodium azide in DMF to give (R)-3-azidotetrahydrofuran which is in turn reduced with Raney Nickel catalysts to obtain finally (R)-3-aminootetrahydrofuran. (Jin, L and Shi, X, Chinese Patent CN 1660829 (2004). Alternatively the resultant mesylate ester mentioned earlier is then reacted with benzyl amine inverting the configuration at the chiral center. The resultant 3-benzylamino-tetrahydrofuran is debenzylated under hydrogenolytic conditions to yield 3-amino tetrahydrofuran. Such sequences are lengthy, yield intermediate stages difficult to purify, involve azide reagents. The synthesis also presents practical difficulties such as isolation of water-soluble intermediates as pointed out earlier. Also the synthesis involves highly corrosive substances such as mesyl chloride. Stereochemically the reactions involve stereoinversions which are not very dependable and may yield partially inverted materials.

In another approach, (Barlos, K; Papaioannou, D; Patrianakou, S; Sanida, C and Tsegenidis, *Chemical Communications*, 1987, 474) L-methionine reduced to the corresponding L-amino alcohol whose amino group is protected with a trityl group. This material is then alkylated with methyl iodide and with the use of a base such as sodium hydride, it is converted to (S)-3-tritylamino-tetrahydrofuran from which (S)-3-amino-tetrahydrofuran is liberated by an acid treatment. This method suffers from the use of trityl group as a protecting group which adds lot of dead weight to the molecule. Also the dimethyl sulfide that is evolved in the cyclization stage is stench and an environmental hazard.

Zhu and Fan describe (Zhu, L and Fan, H, Chinese Patent CN 1814769, 2006) a chemoenzymatic method of making 3-(S)-aminotetrahydrofuran from racemic tetrahydrofuran-3-carboxylic acid. In this method, tetrahydrofuran-3-carboxylic acid is treated with diphenylphosphoryl azide to effect a Curtius rearrangement/degradation, followed by reaction with benzyl alcohol, separation of the intermediate product, namely, N-benzyoxycarbonyl-3-amino-tetrahydrofuran, by column chromatography followed by enatioselective enzymatic hydrolysis using papain. This method suffers from use explosive agents like azides, intermediate formation of reactive isocyanates etc.

Thus there is lack of a good method for the production of chiral 3-amino-tetrahydrofuran.

All the literature cited in this invention refer to relevant literature in this field of activity and these cited work also are incorporated by reference.

DESCRIPTION OF THE PRESENT INVENTION

Amino acids are abundantly and economically available. They are also available in chiral forms. While L-forms are naturally (by fermentation) available, the D-forms are quite easily obtained through asymmetric transformation or resolution.

The present invention uses the inherent chirality present in L-aspartic acid and converts L-aspartic acid in a series of simple, easily executable reactions to (S)-3-amino-tetrahydrofuran in good yields and with complete retention of optical purity. An identical sequence starting from D-aspartic acid leads to the other optically active isomer, namely (R)-3-amino-tetrahydrofuran.

The method starts with L-aspartic acid that is esterified with alcohols such as methanol, ethanol or higher alcohols including benzyl alcohol in acid medium. Typically the process uses dimethyl esters of aspartic acid.

Such a diester, for example, L-aspartic acid dimethyl ester is reacted with acid chlorides such as benzoyl chloride to give solid N-benzoyl-dimethyl-L-asparate in very good yields. In stead of benzoyl chloride, one can use alkanoyl chloride such as acetyl chloride, propionyl chloride, phenyl acetyl chloride etc. Also in addition to simple carboxylic acid chloride, one can also use chlorides of half esters of carbonic acid such as methyl chloroformate, ethyl chloroformate, benzyl chloroformate or t-butyl chlorofomate to produce the corresponding Dimethyl-N-alkoxycarbonyl-L-aspartate as the product.

Generally the following structure embodies one of the preferred starting materials

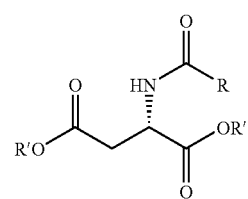

In yet another variation of this strategy, dimethyl ester of L-aspartic acid is reacted with arylsulfonyl chlorides such benzenesulfonyl chloride or p-toluenesulfonyl chloride or p-chlorobenzenesulfonyl chloride or naphthalenesulfonyl chloride to give N-arylsulfonyl-dimethyl aspartate.

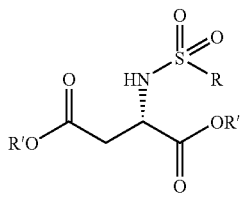

These compounds are easily reduced with metal hydrides such as sodium borohydride, potassium borohydride or lithium borohydride. In addition zinc borohydride also could be used for such reduction to give chiral N-substituted-butane-1,4-diol in good yields and excellent optical purity. Even wider diversity of methods exists for such reduction. Additives such as Indium chloride, Aluminum chloride etc facilitate such reductions. Stronger hydrides such as lithium aluminum hydride under milder conditions also yield the desired 1,4-diols. (Braga, A L; Lüdtke, D S; Sehnem, J A and Alberto, E E; Tetrahedron, 2005, 61 11664)

We discovered that these N-acyl or N-sulfonyl-butane-1, 4-diols could be cyclized easily as neat materials or more beneficially in solvents and such cyclization was catalyzed by acids. The starting material totally disappeared leading to the product. In addition such cyclization could be further facilitated by microwave heating in dipolar solvents. (Topics in Current Chemistry, Vol 266, *Microwave Methods in Organic synthesis*, Volume Editors: Larhead, M and Olofsson, K, Springer, N.Y. 2006) The reaction could be done in solvents such as ethers, diphenylether, or polar solvents such as DMF or DMSO. Specifically such cyclizations could be done in hydrocarbon solvents such as toluene. Such cyclization is catalyzed by Bronsted acids, for example p-toluenesulfonic acid.

For example, as illustrated in one of the following examples, (S)-3-benzoylamino 1,4-butanediol is cyclized to 3-benzoylaminotetrahydrofuran at relatively low temperatures. We speculate that this cyclization goes through an intramolecularly catalyzed cyclization as depicted below.

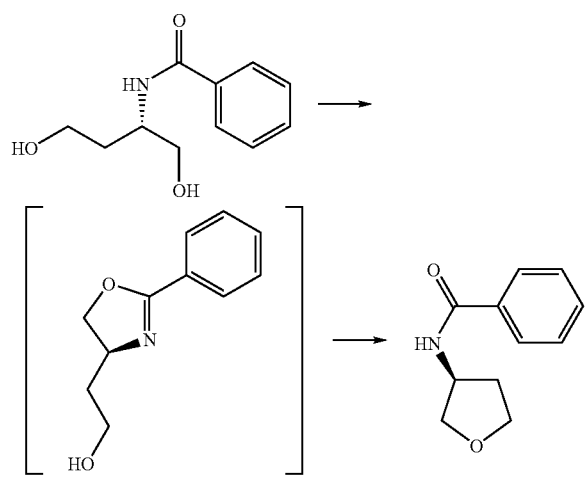

Such speculative theories notwithstanding, the invention described in the present disclosure leads to racemization-free cyclization to 3-benzoylaminotetrahydrofuran.

The complete retention of chirality in the product was demonstrated by chiral HPLC analysis.

Once the cylclization is complete, the protecting group on the nitrogen center is removed by hydrolysis (acid or base), reductive removal with metals or by hydrogenolytic removal depending on the group that is employed. For example in the case of benzoyl group as shown above, the removal of benzoyl group is effected by basic or acidic hydrolysis and the product can be isolated as white, crystalline hydrochloride salt. The product could also be isolated as amino compound and could be purified further by distillation. It also forms a crystalline salt with p-toluenesulfonic acid.

In the case of sulfonyl protecting groups, a mild, reductive removal of the sulfonyl group can also employed. (Grehn, L and Ragnarsson, U; *J Organic Chem.*, 2002, 67, 6557)

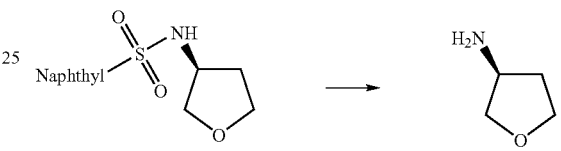

The following examples exemplify the practice of this invention but do not set any limitations on the invention.

EXAMPLE 1

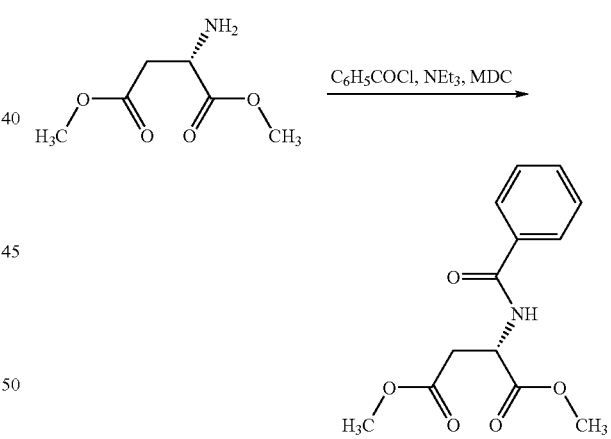

Dimethyl-L-aspartate (74.0 g) was suspended in methylene dichloride (MDC) and cooled to 0-10° C. Triethylamine (114 ml) was added slowly over a period of 1 hour followed by benzoyl chloride (51 ml). The reaction mixture was stirred at RT for 3 hours at which time TLC showed the absence of starting material. Reaction mixture was quenched in water and MDC layer separated. It was washed with 5% $NaHCO_3$ solution, then with water and dried over anhydrous sodium sulfate. MDC layer was concentrated completely and diethyl ether was added and stirred for complete precipitation. The resultant required product was dried under vacuum.

Yield: 66 g

EXAMPLE 2

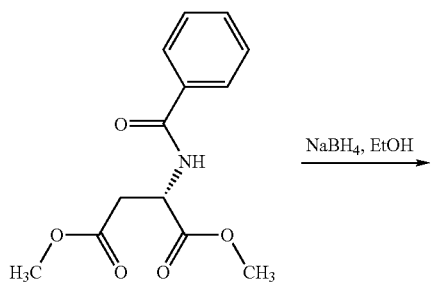

N-Benzoyl-dimethyl L-aspartate (66.0 g) dissolved in THF and Ethanol (~260 ml each). It was cooled to 10-15° C. NaBH₄ was added in portion-wise and stirred at room temperature for 1 hour. Then it was heated to reflux for 8-9 hours. TLC showed only traces of starting material. The reaction mixture was cooled to 0-10° C. and adjusted the pH to 7 with dilute HCl and extracted with ethylacetate three times. The organic extract was dried over anhydrous sodium sulfate and then was concentrated to get a white solid. The solid was stirred with diethyl ether, filtered, washed and dried at room temperature under vacuum.

Yield: 35 g; Enantiomeric purity was established by chiral HPLC (Chirobiotic Tag®—Eluent 80:20—hexane: ethanol): Specific rotation $[\alpha]_D=-27.7°$ C. (c=3.4, MeOH)

EXAMPLE 3

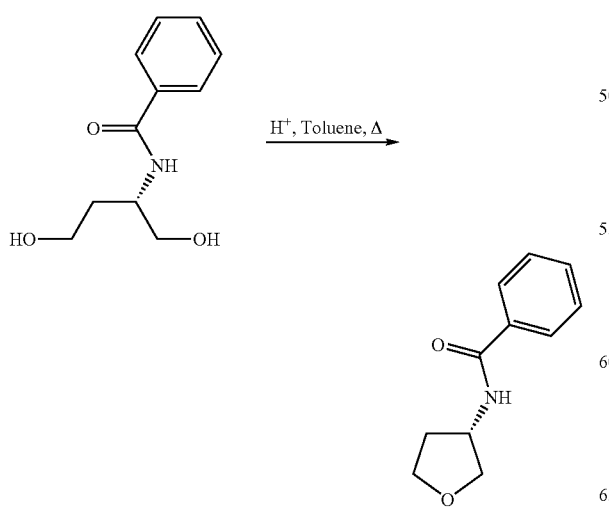

N-Benzoylamino 1,4-butane diol (35 g, 0.167 mol) was taken in a round-bottom flask in toluene (350 ml) and p-toluenesulfonic acid (3.5 g). The reaction was heated to reflux for 10-12 hours. With the help of Dean-Stark apparatus, water was removed azeotropically. The reaction mixture was quenched in water, extracted with ethylacetate dried over sodium sulfate. It was then concentrated completely and purified by column chromatography. Yield: 20 g, Specific rotation $[\alpha]_D$: -23° (C=3.4, Methanol). Proton NMR (DMSO Solvent, 300 MHZ): 8.57-8.60 (1H), 7.85-7.89 (2H), 7.42-7.59 (3H), 4.40-4.50 (1H), 3.80-3.90 (2H), 3.68-3.77 (1H), 3.56-3.60 (1H), 2.09-2.20 (1H), 1.87-2.00 (1H)

EXAMPLE 4

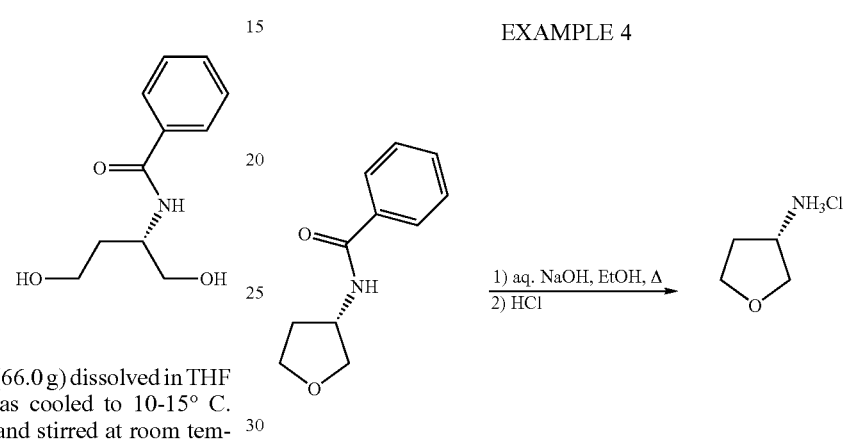

3-N-benzoylamino-tetrahydrofuran (20.0 g) was dissolved in Ethanol (~75 ml) and sodium hydroxide solution (50 g sodium hydroxide in 100 ml water) was added. The reaction mixture was heated to reflux for 9-10 hours. TLC showed absence of starting material. The reaction mixture was cooled to room temperature and was acidified with dil HCl till acidic $p^H$. Precipitated benzoic acid was filtered. The aqueous layer washed with MDC and concentrated completely to get the material which is occluded with salt. Isopropanol was added and stirred for 1 hr at room temp. Salt was filtered and the reaction mass concentrated completely to get a pasty mass. It was then stirred with IPA to crystallize out the material. It was then washed with chilled IPA and dried under vacuum. Yield: 111 g

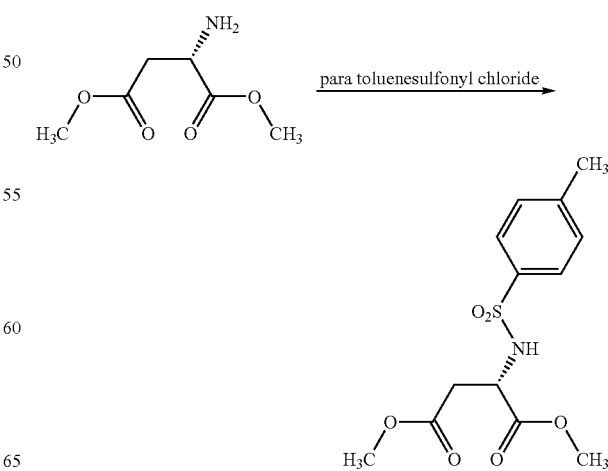

EXAMPLE 5

The reaction was performed under similar conditions described in example 1; The product isolated formed the input for example 6

EXAMPLE 6

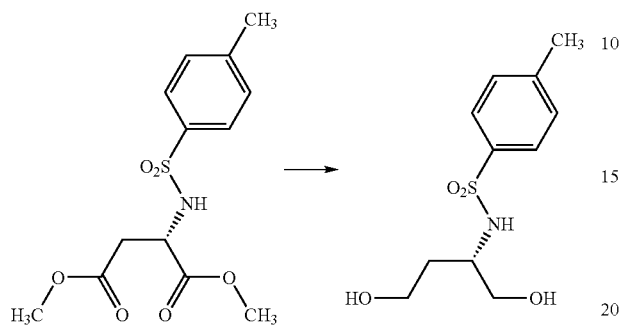

This reaction was performed under similar conditions described under example 2

EXAMPLE 7

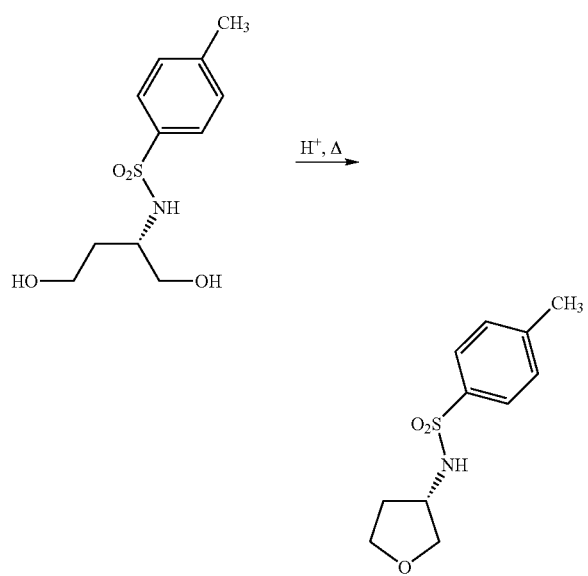

The cyclization reaction was performed under conditions described in example 3

EXAMPLE 8

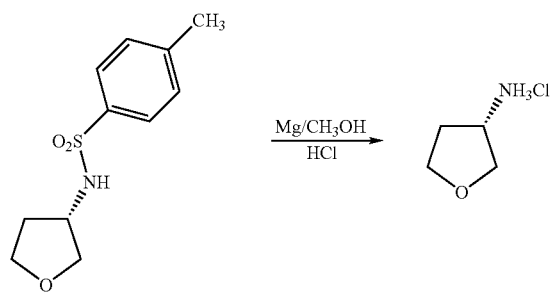

The deprotection was performed using magnesium/methanol protocol. A similar reaction with 2-naphthalenesulfonyl chloride was performed with better yield

What is claimed is:

1. A process for the manufacture of 3-(S)-aminotetrahydrofuran comprising the steps of
   a) reduction of a compound with structure I to a compound with structure II with the aid of a hydride reducing agent;

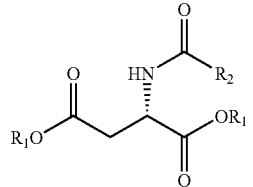

I

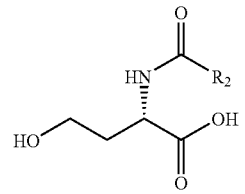

II

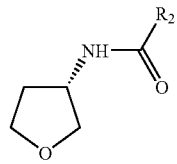

III wherein $R_1$ is selected from the group consisting of $C_1$-$C_6$ straight chain and branched alkyls and —$CH_2$-Aryl; $R_2$ is selected from a group consisting of $C_1$-$C_6$ straight chain and branched alkyls, —$CH_2$-Aryl, phenyl and substituted phenyl;
   b) cyclizing the compound with structure II with the aid of sulfonic acids to structure III;
   c) hydrolyzing the compound using a base with structure III to 3-(S)-aminotetrahydrofuran; and
   d) recovering 3-(S)-aminotetrahydrofuran as its hydrochloride or p-toluenesulfonate salt or as base itself.

2. A process as claimed in claim 1 wherein the reducing agent is chosen from the group consisting of sodiumborohydride, potassiumborohydride, lithiumbodohydride, zincborohydride and lithium aluminum hydride.

3. A process as claimed in claim 1 wherein the acid used in cyclizing compound II to give compound III is chosen from the group of acids comprising benzenesulfonic acid, p-toluenesulfonic acid, naphthalenesulfonic acid, methane sulfonic acid and fluorosulfonic acid.

4. A process as claimed in claim 1 wherein the base to hydrolyze compound III to 3-(S)-aminotetrahydrofuran is chosen from a group comprising sodium hydroxide, potassium hydroxide and barium hydroxide.

5. A process for the manufacture of 3-(S)-aminotetrahydrofuran comprising the steps of:
   a) reduction of a compound with structure IV to a compound with structure V wherein $R_1$ is selected from the group consisting of $C_1$-$C_6$ straight chain and branched

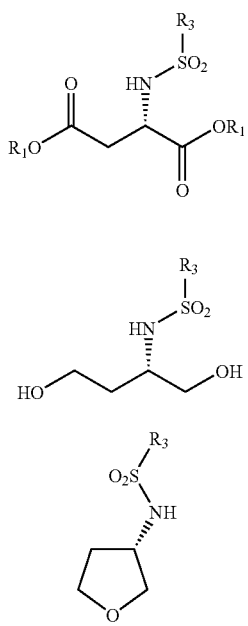

alkyls and —CH$_2$-Aryl; R$_3$ is selected from a group consisting of phenyl, substituted phenyl, 1-naphthyl, and 2-naphthyl with the aid of a hydride reducing agent;

b) cyclizing the compound with structure V with the aid of sulfonic acids to structure VI;

c) reductively cleaving compound VI to 3-(S)-aminotetrahydrofuran; and d) Recovering 3-(S)-aminotetrahydrofuran as its hydrochloride or p-toluenesulfonate salt or as base itself.

6. A process as claimed in claim 5 wherein the reducing agent is chosen from the group consisting of sodiumborohydride, potassiumborohydride, lithiumbodohydride, zincborohydride and lithium aluminum hydride.

7. A process as claimed in claim 5 wherein the acid used in cyclizing compound V to give compound VI is chosen from the group of acids comprising benzenesulfonic acid, p-toluenesulfonic acid, naphthalenesulfonic acid, methane sulfonic acid and fluorosulfonic acid.

8. A process as claimed in claim 5 wherein compound VI is reductively cleaved using a metal chosen from the group consisting of sodium, potassium, zinc and magnesium in a medium chosen from the group consisting of methanol and ethanol.

\* \* \* \* \*